United States Patent [19]

Balke et al.

[11] 4,111,976

[45] Sep. 5, 1978

[54] PROCESS FOR THE PREPARATION OF METHYLIMINOISOBUTYRATE HYDROCHLORIDE

[75] Inventors: David E. Balke; Donald E. Perez, both of Mobile, Ala.

[73] Assignee: Ciba-Geigy Corporation, Ardsley, N.Y.

[21] Appl. No.: 865,099

[22] Filed: Dec. 27, 1977

[51] Int. Cl.$^2$ ............................................. C07C 119/18
[52] U.S. Cl. ............................................. 260/453 RW
[58] Field of Search ............................... 260/453 RW

[56] References Cited

U.S. PATENT DOCUMENTS 2,553,564  5/1951  Fein et al. .................. 260/453 RW

*Primary Examiner*—Lewis Gotts
*Assistant Examiner*—Robert C. Whittenbaugh
*Attorney, Agent, or Firm*—Karl F. Jorda

[57] ABSTRACT

A process is provided for preparing methyliminoisobutyrate hydrochloride by reacting isobutyronitrile (IBN), hydrogen chloride (HCl) and methanol in the presence of excess HCl, wherein the IBN and HCl are added at a temperature from about 5° C to about 25° C to a methanolic solution containing excess HCl and by maintaining during the reaction a methanolic reaction medium saturated with HCl.

9 Claims, No Drawings

PROCESS FOR THE PREPARATION OF METHYLIMINOISOBUTYRATE HYDROCHLORIDE

FIELD OF THE INVENTION

This invention relates to iminoethers used as intermediates for various chemical reactions, e.g., for conversion with ammonia to amidines which are starting materials for the preparation of pyrimidine derivatives. Thus, thioesters of 6-hydroxypyrimidine derivatives have become known as insecticidally and acaricidally active agents in the pest control area and are disclosed and claimed in U.S. Pat. No. 2,754,243. A typical example of those derivatives is O,O-diethyl-O-(2-isopropyl-4-methyl-6-pyrimidyl)thiophosphate which has become a well-established commercial product under the trademark DIAZINON ®.

BACKGROUND OF THE INVENTION

In accord with the literature, the process for preparing iminoethers as intermediate products may be described by the following general equation, starting with a corresponding nitrile:

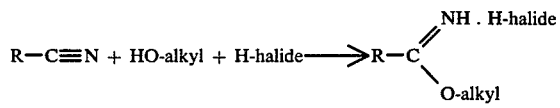

in which R represents an organic residue, such as, for example, a lower alkyl group; HO-alkyl stands for a lower alkanol and H-halide means hydrochloric or hydrobromic acid. As shown, the iminoethers are obtained in the form of salts. Very often this fact results in an undesirable precipitation during the batch reaction or the continuous process for preparing them. If this occurs, the manufacturing process is adversely affected because for completion of the reaction or for subsequent reactions, e.g., with ammonia, the reaction partners should be present in a homogeneous solution. Furthermore, the process of forming iminoethers is exothermic and must be accomplished by cooling. Crystallization of the salt, however, is an additional exothermic phenomenon which might occur within a very short period of time. In addition, an immediate overheating of the reaction mixture very often runs out of control.

Heretofore, 2-isopropyl-4-methyl-6-hydroxy pyrimidine was prepared by treating ethyliminoisobutyrate hydrochloride with ammonia to obtain the amidine of the formula

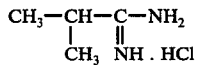

and reacting the latter with methylacetoacetate. Ethyliminoisobutyrate hydrochloride has been manufactured according to the equation given at the outset starting with isobutyronitrile (IBN), hydrogen chloride (HCl) and ethanol. However, though it appeared highly desirable to replace ethanol by the less expensive methanol in the iminoether process inasmuch as the latter could simultaneously be used as solvent and more easily distilled off due to its lower boiling point, it had heretofore not been done because in practice it was found that methyliminoisobutyrate hydrochloride precipitated very readily during the reaction and under normal reaction conditions in the range of 15° to 25° C. about equimolar amounts of IBN, methanol and HCl led to crystallization of the final product during the reaction with all of the disadvantages as outlined above.

DETAILED DISCLOSURE

The present invention is directed to a process for improved manufacture of methyliminoisobutyrate hydrochloride of the formula I

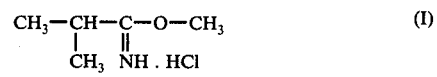

which is kept dissolved during and after the reaction to provide a homogeneous reaction mixture suitable for further reactions. This result is achieved by maintaining a critical relationship of alkanonitrile, hydrogen halide and methanol in a given temperature range.

More specifically, this invention is concerned with the surprising discovery that hydrogen halide is a critical parameter for preventing the precipitation of this iminoether during the reaction. Hydrogen halide used in excess over the necessary amounts to carry out the reaction favors the solubility of the final product in the reaction mixture.

In greater detail, the invention is directed to a process for preparing methyliminoisobutyrate hydrochloride of formula I of high yield and purity by reacting IBN, HCl and methanol in the presence of excess HCl and to the improvement therein which comprises adding the IBN and HCl at a temperature of from about 5° to 25° C. to a methanolic solution containing excess HCl and maintaining during reaction a methanolic reaction medium saturated with HCl. Depending on the cooling conditions, the reaction may be carried out in the range of from about 5° to 10° C., of from about 10° to 15° C. or of from about 15° to 25° C. Within the latter range, a preferred temperature is from about 20° to 25° C.

Most particularly, the invention pertains to an improved process which comprises adding at a temperature range of about 5° to about 25° C. the IBN and HCl to an at least equimolar amount of methanol saturated with HCl and further maintaining during the reaction a methanolic medium wherein the relationship of HCl addition rate, IBN addition rate and temperature corresponds to (a) at least 1.0 mole HCl per hour and per mole IBN at a range of from about 5° to 10° C.,
(b) at least 1.5 moles HCl per hour and per mole IBN at a range of from about 10° to 15° C.,
(c) at least 1.9 moles HCl per hour and per mole IBN at a range of from about 15° to 25° C., a preferred temperature range being from about 20° to 25° C.

Under the conditions of the process, the temperature may be raised over 25° C.; it should however be maintained under 30° C. For reasons of high yields and excellent purity of the final compound I, it is advisable to keep the temperature of the exothermic reaction below 25° C. The temperature may also be lowered down to 0° C. However, this requires additional cooling devices without concommitant advantages.

According to reaction condition (c) above, an addition rate of from 2.0 to 2.3 moles HCl per hour and per mole IBN is a preferred embodiment, and may preferably be used at temperatures of from 20° to 25° C.

An especially preferred embodiment consists in an addition rate of from 2.0 to 2.1 moles HCl per hour and per mole IBN, preferably used at temperatures of from 20° to 25° C.

The reaction conditions of this invention described herein can be used either for a batch process or for a continuous process.

HCl is not only a critical parameter for avoiding precipitation of compound of formula I during the reaction but can additionally be used where precipitation occurs as a result of faulty temporary excess in isobutyronitrile input. In the initial phase of solidification, the crystals of compound I can easily be dissolved by interrupting the IBN input while maintaining the addition of HCl.

The following data and example will serve to illustrate an improved process of manufacture of iminoether of high yield and purity which are kept dissolved during and after the reaction to provide a homogeneous reaction mixture ready for further operation, and which is affected by maintaining a critical relationship of alkanonitrile, hydrogen halide and alcohol in a given temperature range. It will be understood, however, that it is not intended that the invention be limited to the particular embodiments disclosed. Various modifications thereof can be employed and will be readily apparent to those skilled in the art.

EXAMPLE

To a 1-liter 5-neck round-bottom flask equipped with an agitator, thermometer, subsurface HCl gas feed tube with gas rotameter and vent gas sulfuric acid bubbler, 138 g of methanol (4.32 moles — 8% excess over theory) was charged.

The reaction mass was agitated and HCl gas was added through the rotameter for 30 minutes until the alcohol was saturated with HCl. The reaction was maintained at 20°-25° C. by using an acetone-dry ice bath. HCl gas flow was adjusted to avoid either violent bubbling of excess gas through the vent bubbler, or a vacuum formation resulting in sulfuric acid being sucked up into the vent tube. After the 30 minutes of HCl gas feed, a dropwise feed of 276 g of isobutyronitrile (4 moles) was started and the nitrile was added at a constant rate over a 3 hour period. The HCl flow was continued throughout the nitrile addition as well as for 30 minutes after all of the nitrile had been added for a total addition of 305 g of HCl. The reaction mass temperature was maintained at 20°-25° C. throughout the HCl and nitrile addition. After all HCl had been added, agitation of the reaction mass was continued for 2 hours.

The resultant reaction mass consisted of about 76% methyliminoisobutyrate hydrochloride and 21% unreacted HCl. The balance of the composition was methanol and a small quantity of impurities.

As shown in Table 1, the following amounts of IBN and HCl have been found to fulfill the minimum conditions of avoiding crystallization of compound I at the temperature range of 20° C. to 25° C.

Table 1

| Cumulative IBN Fed | Minimum Cumulative HCl Fed |
|---|---|
| 2 parts by weight | 2.21 parts by weight |
| 4 parts by weight | 4.43 parts by weight |
| 6 parts by weight | 6.65 parts by weight |
| 8 parts by weight | 8.87 parts by weight |
| 10 parts by weight | 11.09 parts by weight |
| 12 parts by weight | 13.31 parts by weight |

In accordance with the teaching of this invention, as shown in Table 2, the following data corroborate the necessity of an HCl excess during the reaction to avoid precipitation of methyliminoisobutyrate hydrochloride.

Table 2

| Batch Size (Moles IBN) | Temp. (0° C) | Moles HCl Hour · Mole IBN | Crystallization Yes | Crystallization No |
|---|---|---|---|---|
| 4 | 5-10 | 0.98 | | x |
| 4 | 6-10 | 1.17 | | x |
| 4 | 5-9 | 1.12 | | x |
| 4 | 10-14 | 1.09 | x | |
| 4 | 15-20 | 1.08 | x | |
| 4 | 20-25 | 0.85 | x | |
| 4 | 20-25 | 1.23 | x | |
| 2 | 21-24 | 1.09 | x | |
| 4 | 20-25 | 2.10 | | x |
| 12 | 20-25 | 2.11 | | x |

What is claimed is:

1. In the process for preparing methyliminoisobutyrate hydrochloride of the formula

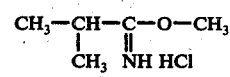

by reacting isobutyronitrile, hydrogen chloride and methanol in the presence of excess hydrogen chloride, the improvement which comprises adding the isobutyronitrile and hydrogen chloride at a temperature of from about 5° to 25° C. to a methanolic solution containing excess hydrogen chloride and maintaining during the reaction a methanolic reaction medium saturated with hydrogen chloride.

2. A process according to claim 1, wherein the temperature is in the range of from about 5° to 10° C.

3. A process according to claim 1, wherein the temperature is in the range of from about 10° C. to 15° C.

4. A process according to claim 1, wherein the temperature is in the range of from about 15° to 25° C.

5. A process according to claim 1, wherein the temperature is in the range of from about 20° to 25° C.

6. In the process for preparing methyliminoisobutyrate hydrochloride of the formula

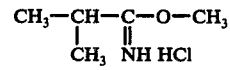

by reacting isobutyronitrile, hydrogen chloride and methanol in the presence of excess hydrogen chloride, the improvement which comprises adding at a temperature range of about 5° to 25° C. isobutyronitrile and hydrogen chloride to methanol saturated with hydrogen chloride and further maintaining during the reaction a methanolic medium wherein the relationship of hydrogen chloride addition rate, IBN addition rate and temperature corresponds to
   (a) at least 1.0 mole hydrogen chloride per hour and per mole isobutyronitrile at a range of from about 5° to 10° C.
   (b) at least 1.5 moles hydrogen chloride per hour and per mole isobutyronitrile at a range of about 10° and 15° C., and
   (c) at least 1.9 moles hydrogen chloride per hour and per mole isobutyronitrile at a range of about 15° to 25° C.

7. A process according to claim 6, wherein the temperature is at a range of about 20° to 25° C.

8. A process according to claim 7, wherein the addition rate corresponds to 2.0 and 2.3 moles hydrogen chloride per hour and per mole isobutyronitrile.

9. A process according to claim 7, wherein the addition rate corresponds to 2.0 to 2.1 moles hydrogen chloride per hour and per mole isobutyronitrile.

* * * * *